(12) United States Patent
Chen et al.

(10) Patent No.: US 11,413,237 B2
(45) Date of Patent: *Aug. 16, 2022

(54) SKIN PENETRATION ENHANCING COMPOSITION AND USE THEREOF IN PREPARATION OF SKIN DELIVERY FORMULATION

(71) Applicant: Xiamen University, Fujian (CN)

(72) Inventors: Ming Chen, Fujian (CN); Dexiang Wang, Fujian (CN); Chunyun Liu, Fujian (CN); Saiman Zhang, Fujian (CN); Chi Zhang, Fujian (CN)

(73) Assignee: Xiamen University, Xiamen (CN)

( * ) Notice: Subject to any disclaimer, the term of this patent is extended or adjusted under 35 U.S.C. 154(b) by 86 days.

This patent is subject to a terminal disclaimer.

(21) Appl. No.: 17/052,999

(22) PCT Filed: Feb. 26, 2018

(86) PCT No.: PCT/CN2018/077288
§ 371 (c)(1),
(2) Date: Nov. 4, 2020

(87) PCT Pub. No.: WO2019/029154
PCT Pub. Date: Feb. 14, 2019

(65) Prior Publication Data
US 2021/0121394 A1    Apr. 29, 2021

(30) Foreign Application Priority Data
Aug. 7, 2017  (CN) .......................... 201710666564.2

(51) Int. Cl.
| A61K 8/98 | (2006.01) |
| A61K 8/02 | (2006.01) |
| A61K 8/04 | (2006.01) |
| A61K 8/14 | (2006.01) |
| A61K 9/00 | (2006.01) |
| A61K 9/14 | (2006.01) |
| A61K 47/46 | (2006.01) |
| A61Q 19/00 | (2006.01) |

(52) U.S. Cl.
CPC ............ *A61K 8/987* (2013.01); *A61K 8/0245* (2013.01); *A61K 8/0279* (2013.01); *A61K 8/0291* (2013.01); *A61K 8/044* (2013.01); *A61K 8/14* (2013.01); *A61K 9/0014* (2013.01); *A61K 9/14* (2013.01); *A61K 47/46* (2013.01); *A61Q 19/00* (2013.01); *A61K 2800/10* (2013.01); *A61K 2800/413* (2013.01)

(58) Field of Classification Search
None
See application file for complete search history.

(56) References Cited

U.S. PATENT DOCUMENTS

| 2004/0055957 A1 | 3/2004 | Palm et al. |
| 2004/0109872 A1 | 6/2004 | Villni |
| 2018/0311143 A1* | 11/2018 | Chen ..................... A61M 37/00 |

FOREIGN PATENT DOCUMENTS

| CN | 101209251 A | 7/2008 |
| CN | 101626775 A | 1/2010 |
| CN | 105858669 A | 8/2016 |
| CN | 105999535 A | 10/2016 |
| CN | 106413723 A | 2/2017 |
| CN | 110882219 A | 3/2020 |
| CN | 111012916 A | 4/2020 |
| KR | 101323613 B1 | 11/2013 |
| WO | 2008043071 A2 | 4/2008 |
| WO | 2015156455 A1 | 10/2015 |

OTHER PUBLICATIONS

Zhang et al., "Skin Delivery of Hydrophilic Biomacromolecules Using Marine Sponge Spicules", .Mol. Pharmaceutics, 2017, 14, 9, 3188-3200 (published: Aug. 1, 2017). (Year: 2017).*
Larrañeta et al., "Microneedles: A New Frontier in Nanomedicine Delivery", Pharm Res, 2016, 33, pp. 1055-1073. (Year: 2016).*
Li Li, Fang Liang, "Research Progress in the Application of Nano-drug Carriers in Transdermal Drug Delivery Systems", and English Abstract, Journal of Shenyang Pharmaceutical University, vol. 27, Issue 12, Dec. 20, 2010 (Dec. 20, 2010), pp. 998-1002.
International Search Report with English Translation, cited in PCT/CN2018/077288 dated May 24, 2018, 6 pages.
Written Opinion with English Translation cited in PCT/CN2018/077288 dated May 24, 2018, 7 pages.
"An Introduction to the Study on Natural Characteristics of Sponge spicules and Bionic Applications", Oct. 2006, Wang et al., Advanced in Earth Science, vol. 21, Issue 10, 7 pgs.
"Skin Delivery of Hydrophilic Biomacromolecules Using Marine Sponge Spicules", Aug. 2017, Saiman Zhang, Huilong Ou, Chunyun Liu, Yuan Zhang, Samir Mitragotri, Dexiang Wang and Ming Chen, American Chemical Society, Molecular Pharmaceutics, 13 pgs.
"Monthly Variations in the Size of Spicules of the Haplosclerid Sponge, Haliclona Rosea (Bowerbank)", 1991, W.C. Jones, In: Reitner J., Keupp H. (eds) Fossil and Recent Sponges, Springer, Berlin, Heidelberg, 17 pgs.
First Chinese Office Action cited in CN Application No. 201610267935.5 dated Nov. 1, 2018, 19 pgs.
Second Chinese Office Action cited in CN Application No. 201610267935.5 dated Apr. 16, 2019, 16 pgs.
"Design and Evaluation of Skin Delivery System of Docetaxel", Aug. 2009, Yu-Qin Qiu, China Academic Journal Electronic Publishing House, 132 pgs.

* cited by examiner

*Primary Examiner* — Melissa L Fisher
(74) *Attorney, Agent, or Firm* — Cooper Legal Group, LLC

(57) ABSTRACT

The present disclosure discloses a skin penetration enhancing composition and a use thereof in preparation of a skin delivery formulation. The skin penetration enhancing composition comprises sponge spicules and nanoparticles. The nanoparticles comprise at least one of one or more drugs or one or more cosmetic active ingredients.

12 Claims, 18 Drawing Sheets

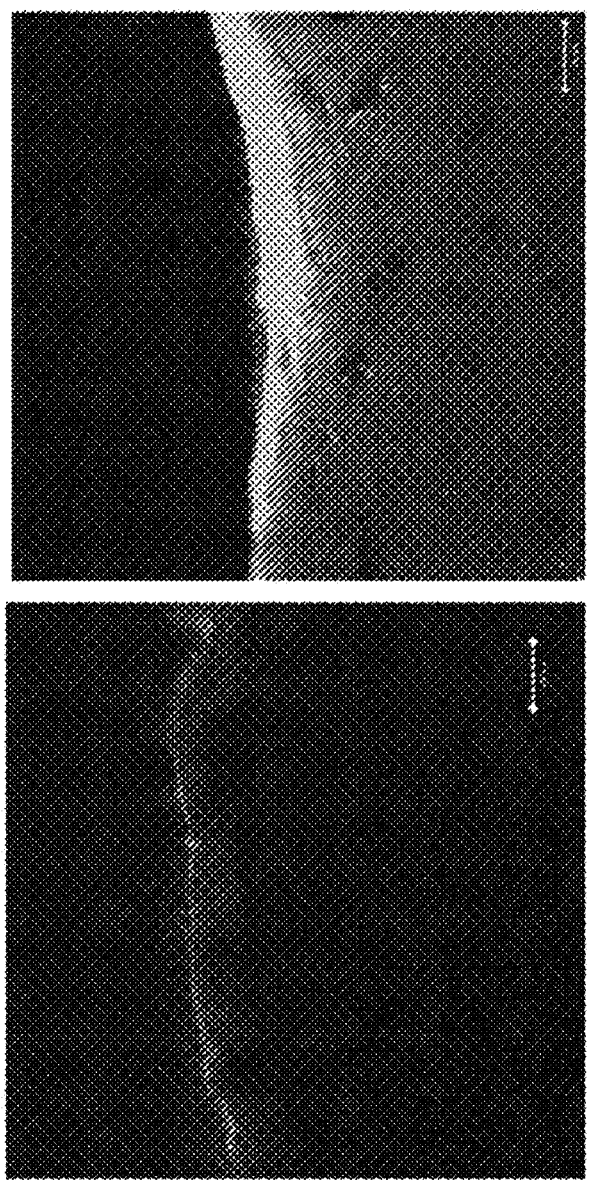
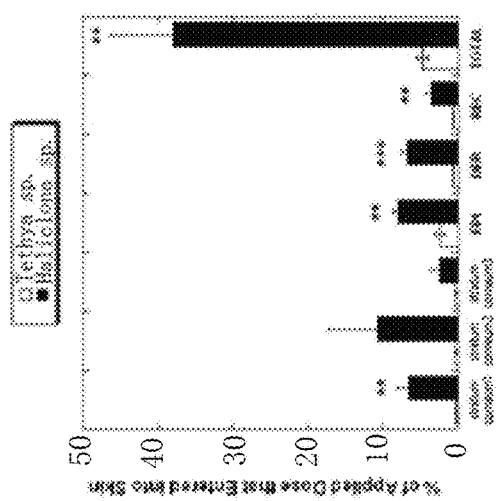
Fig. 17A
Fig. 17B
Fig. 17C

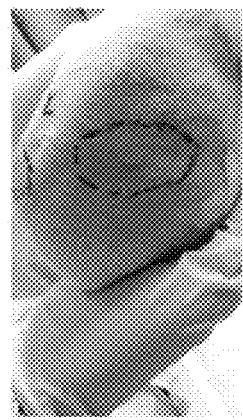 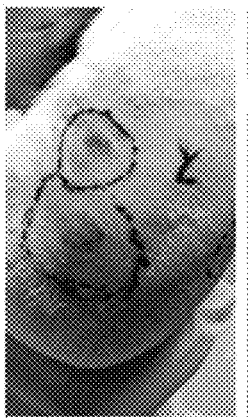 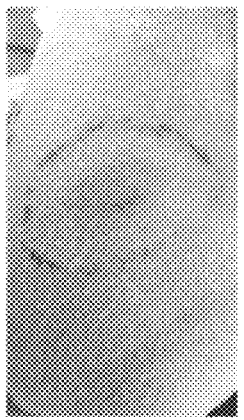 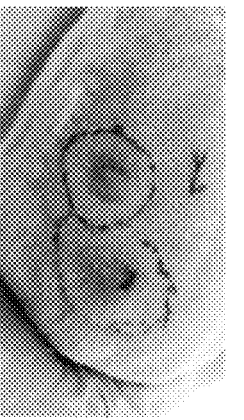
Fig. 18A  Fig. 18B  Fig. 18C  Fig. 18D
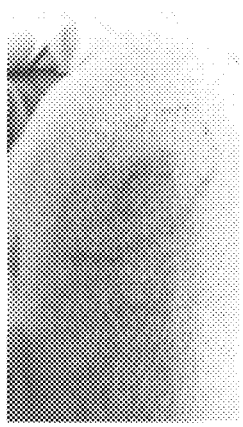 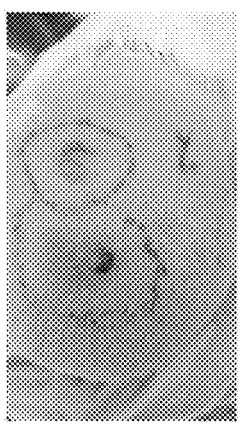 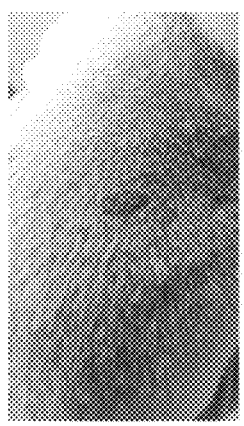 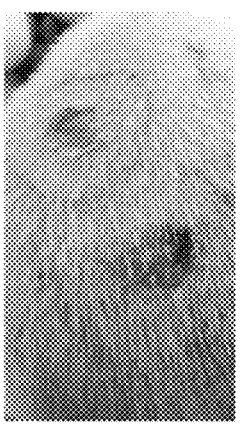
Fig. 18E  Fig. 18F  Fig. 18G  Fig. 18H
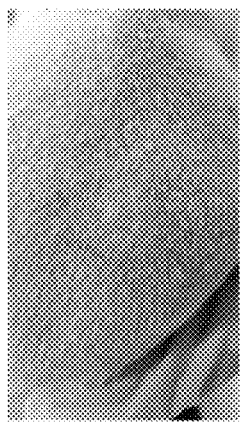 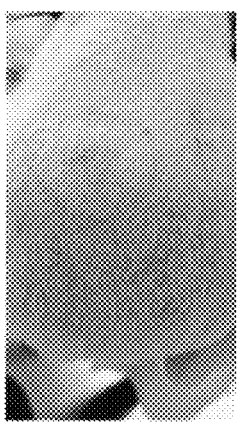 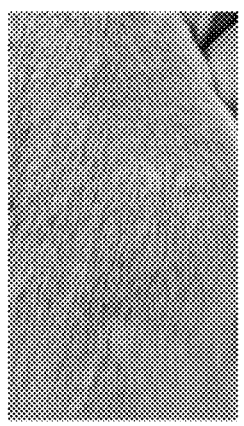 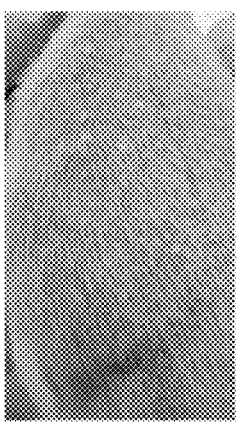
Fig. 18I  Fig. 18J  Fig. 18K  Fig. 18L

SKIN PENETRATION ENHANCING COMPOSITION AND USE THEREOF IN PREPARATION OF SKIN DELIVERY FORMULATION

FIELD OF THE DISCLOSURE

The disclosure relates to the field of skin drug delivery, and in particular to a skin penetration enhancing composition and its use thereof in preparation of a skin delivery system. Sponge spicules, which are a kind of physical skin penetration enhancer, are utilized in combination with different types of nanoparticles to increase the skin penetration and deposition of drugs or cosmetic active ingredients.

BACKGROUND OF THE DISCLOSURE

Skin is the largest organ of the human body and offers a direct route for administration of drugs and cosmetic active ingredients. From a pharmaceutical point of view, skin delivery brings forth many advantages over other administration routes (i.e., oral administration and injection administration), including avoiding first-pass metabolism sustained and controlled delivery over a prolonged period of time, reduction in side effects associated with systemic toxicity, direct access to target or diseased site, possibility of visual monitoring of the affected region and the possibility of surgical removal of aberrant tissue if unwanted side effects occur, improved patient acceptance and compliance.

However, skin is a highly defensive barrier in essence against the invasion of external pathogens (i.e., bacteria, fungi, parasites, viruses, heavy metals and various chemical toxins, etc.). In general, only small molecules (i.e., molecular weight <500 Da, 1<log P<2) can penetrate into the skin at therapeutically adequate rates. Most drug molecules, especially biomacromolecules, including polysaccharides, peptides, proteins, nucleic acids, siRNA, etc., are not amenable to skin delivery. Therefore, it is quite challenging to safely and effectively deliver various biomacromolecules drugs and cosmetic active ingredients to deep skin layers.

Currently, penetration enhancing technologies can be generally classified into chemical methods and physical methods. Chemical penetration enhancing methods involve the use of penetration enhancers (i.e., DMSO, azone and pyrrolidone, etc.), peptide penetration enhancers (i.e., skin penetration and cell entering peptide, SPACE peptide, etc.), nanoparticles systems (i.e., liposomes, microemulsions, micelles, carriers, etc.), and so on. While chemical methods are generally low cost, rapid onset, and convenient to use, the application of chemical methods is limited for some reasons, including poor penetration enhancing effects and potential skin irritation or allergies due to the long-term use of chemical penetration enhancers. On the other hand, physical penetration enhancing methods such as iontophoresis, ultrasound, electroporation, thermocautery, laser micro drilling and microneedles, etc. Despite their relatively high efficacy, they require devices with high (e.g., costly) specifications, the design cost and the manufacture cost are quite expensive, and they are not portable. Additionally, a series of problems such as tingling, skin irritation and burning sensation are caused due to their invasive administration methods, so physical penetration enhancing methods can be performed on only small areas of the skin. In addition, the potential application is limited.

Among all the aforementioned enhancement methods, microneedle is a physical penetration enhancing technology that has emerged in recent years, and plenty of microchannels can be created in the skins by minimally invasive methods. Each microneedle has a diameter of 50 to 200 μm and a length ranging from several hundred microns to several millimeters. Microneedles can deep into the epidermis and even to the dermis, while not injuring pain nerves located in the dermis and while providing the most direct and effective way for transdermal absorption. At the same time, the hydrophilic microchannels in skin created by microneedles can enable a series of drugs comprising cosmetic active ingredients, or nanoparticles comprising polysaccharides, peptides, proteins, hormones, vaccines, or other biologically active ingredients to enter into the body. Microneedle technology can be used for the treatment and prevention of skin problems and various diseases. The applications of microneedle technology are very broad, and there are few reports of side effects.

However, due to skin elasticity, the microchannels created by microneedles, such as microneedle rollers or stamps, close up in short time (10-20 min), which limits effective penetration time of drugs, cosmetic active ingredients, or nanoparticles. Currently, microneedle technology is mainly administered in the form of microneedle patches, which have the following disadvantages: long-term use may cause skin irritation and the area of administration of microneedle patches is fixed and small. Although expanding the area of microneedle patches can increase the amount of drug penetrated, it can increase the risk of skin irritation and reduce the compliance of patients. Therefore, microneedle patches are generally only suitable for the skin delivery of small-dose and high active drug, such as insulin or vaccine products. In addition, the sharpness of the microneedle tips and the density of the microneedle arrangement depends on the production and etching production. The requirements are extremely high for preparation materials, preparation processes, and industrialization of the microneedles. Additionally, microneedle patches define an array arrangement and are not well suited for non-flat areas, such as the alar of nose.

Sponge spicules are siliceous or calcareous fibrous substances that function like a skeleton in marine sponges. There are uniaxial, triaxial, and multiaxial types of spicules. Previous research has found that sponge spicules have good optical and mechanical properties. At present, most studies on sponge spicules focus on their nanostructures, optical properties, bionics, etc. However, there are few studies and developments on sponge spicule that naturally have high mechanical strength and sharp ends similar to microneedles. According to the disclosure, sponge spicules can be used as microneedles-like skin penetration enhancers. Compared to traditional microneedles, sponge spicules are dispersed spicules so that they can be topically applied with adapting to any required skin area and location. Further, the application dosage and the method of use (application pressure) of sponge spicules are also flexible with adapting to any skin condition and situation. Moreover, sponge spicules can be retained in the stratum corneum over a long time and create plenty of long-lasting microchannels within skin, which further promotes the percutaneous absorption of biological macromolecules.

However, although the permeability barrier of the skin can be decreased by sponge spicules, the skin permeability of hydrophilic macromolecules is inversely proportional to their molecular weights. For macromolecules with large molecular weight (>50 kDa) or poor physicochemical stability, their topical delivery into the deep skin layer at therapeutically adequate rates is still a big challenge. Therefore, the aim of the present disclosure to develop a more effective strategy for enhancing skin drug delivery.

BRIEF SUMMARY OF THE DISCLOSURE

The present disclosure provides a skin penetration enhancing composition and a use thereof, which overcome the deficiencies of the existing techniques. The skin penetration enhancing composition comprises sponge spicules and nanoparticles. The sponge spicules are utilized with nanoparticles comprising one or more drugs or one or more cosmetic active ingredients synergistically, resulting in an enhanced transdermal absorption of a series of biological macromolecules, such as drugs or cosmetic active ingredients, etc.

A first technical solution adopted by the present disclosure to solve the technical problems is as follows.

A skin penetration enhancing composition comprises sponge spicules and nanoparticles. The nanoparticles comprise at least one of one or more drugs or one or more cosmetic active ingredients.

In a preferred embodiment, the nanoparticles comprise nanocarriers comprising the at least one of the one or more drugs or the one or more cosmetic active ingredients, or the nanoparticles comprise nanosized particles of the at least one of the one or more drugs or the one or more cosmetic active ingredients. In some embodiments, the nanocarriers carried with the at least one of the one or more drugs or the one or more cosmetic active ingredients comprise nanocarriers encapsulating the at least one of the one or more drugs or the one or more cosmetic active ingredients, or nanocarriers attaching with the at least one of the one or more drugs or the one or more cosmetic active ingredients. The nanosized particles of the at least one of the one or more drugs or the one or more cosmetic active ingredients comprise nano-particles directly obtained by pulverizing one or more drugs or one or more cosmetic active ingredients, especially one or more drugs or one or more cosmetic active ingredients of Traditional Chinese Medicine. The nanoparticles disclosed in the present disclosure can be prepared according to existing preparation methods unless otherwise specified.

In a preferred embodiment, the nanocarriers comprise at least one of nanoliposomes, solid lipid nanoparticles, nanocapsules, nanospheres, polymer micelle, or nanosuspensions. Nanoliposomes are nano-particles prepared by encapsulating with membrane materials (bilayers of lipids, such as phospholipids, or cholesterol, etc.). The particle sizes of the nanoliposomes range from 1 nm to 1 µm with unilamellar or multilamellar structure. The solid lipid nanoparticles are solid particles prepared by a plurality of lipid materials (i.e., fatty acid, fatty alcohol, or phospholipid, etc.), and the plurality of lipid materials are solid at room temperature. The nanocapsules and the nanospheres are prepared from biodegradable polymer materials (i.e., polylactic acid, polylactide glycolide, chitosan, gelatin, etc.), or the nanocapsules and the nanospheres can be prepared from non-biodegradable ethyl cellulose ethoce, acrylic resin, etc. Polymer micelles are prepared by dissolving water-soluble block copolymers or graft copolymers in water. The water-soluble block copolymer or the graft copolymer is at least one of polylactic acid-polyethylene glycol block copolymer, chitosan, polylactic acid-glycolic acid (PLGA) block copolymer, etc. Nanosuspensions are prepared by pulverizing drugs in a presentation of additives, such as surfactants or water.

In a preferred embodiment, the nanoliposomes comprise conventional nanoliposomes (CL), flexible nanoliposomes (FL), or ethosomes. The flexible nanoliposomes are prepared by adding a surfactant in a preparation process of conventional nanoliposomes, and the flexible nanoliposomes have a high deformability. Ethosomes are prepared by adding ethanol with a higher concentration in a preparation process of conventional nanoliposomes.

In a preferred embodiment, the sponge spicules are derived from sponge *Haliclona* sp.

In a preferred embodiment, the sponge spicules have a purity configured to be used for skin administration, and the purity of the sponge spicules is not less than 90%, for example, 95% or more, 98% or more, 99% or more, etc. Shapes of the sponge spicules are uniform and structures of the sponge spicules are integrated.

In a preferred embodiment, the sponge spicules are suspended in a solution to obtain a sponge spicules suspension, and the sponge spicules suspension cooperates with the nanoparticles. The sponge spicules suspension is prepared by at least one of a buffer solution, deionized water, double distilled water, or physiological saline, and a mass concentration of sponge spicules is 0.01 to 100%. For example, 0.01%, 0.05%, 0.1%, 0.5%, 1%, 5%, 10%, 20%, 40%, 60%, 80%, or 100%. The buffer solution is, for example, a Phosphate-buffered saline (PBS) solution buffer solution having a molar concentration of 0.01M-0.2 M (Mol/L) and a pH value of 4-9.

A second technical solution of the present disclosure is as follows.

A use of the skin penetration enhancing composition in preparation of a skin delivery formulation.

In a preferred embodiment, the skin delivery formulation is prepared by using the sponge spicules and the nanoparticles. For example, in some embodiments, the sponge spicules and the nanoparticles are respectively prepared according to a method provided by the present disclosure. In some embodiments, the sponge spicules and the nanoparticles are respectively prepared according to a method in preparation of existing drugs and existing cosmetic active ingredients. In some embodiments, the sponge spicules and the nanoparticles are prepared by a method in preparation of existing drugs and existing cosmetics after mixing the sponge spicules and the nanoparticles together. In some embodiments, the skin delivery formulation is prepared by a method in preparation of existing drugs and existing cosmetic active ingredients after respectively adding additives into the sponge spicules and the nanoparticles. In some embodiments, the skin delivery formulation is prepared by a method in preparation of existing drugs and existing cosmetic active ingredients after mixing additives, the sponge spicules, and the nanoparticles.

In a preferred embodiment, the use comprises applying the sponge spicules on skin which has been cleaned, and then applying the nanoparticles on the skin treated with sponge spicules. In some embodiments, the use comprises first applying the sponge spicules on skin which has been cleaned, massaging by hand or by an electric massager with a controlled massage pressure and duration time, then removing residual sponge spicules on the skin by using a buffer solution, deionized water, double distilled water, or physiological saline, and next applying the nanoparticles onto the skin treated with sponge spicules.

In a preferred embodiment, the use comprises applying sponge spicules and nanoparticles of the skin delivery formulation synchronously on skin which has been cleaned, and further massaging by hand or by an electric massager with a controlled massage pressure and duration time for better skin absorption of drug or cosmetic active ingredients.

In present disclosure, the drugs comprise at least one of a drug monomer, a pharmaceutically acceptable salt of a drug monomer, a composition of at least two drug monomers with the same pharmaceutical effects or different pharmaceutical effects, a composition of a drug monomer and a pharmaceutically acceptable salt of a drug monomer with the same pharmaceutically effects or different pharmaceutical effects, or a composition of at least two pharmaceutically acceptable salts of drug monomers with the same pharmaceutical effects or different pharmaceutical effects.

The pharmaceutically acceptable salt is a salt configured to remain pharmaceutical activities and properties of a parent compound. For example, in some embodiments, the pharmaceutically acceptable salt comprises at least one of pharmaceutical metal salt, pharmaceutical ammonium salt, pharmaceutical organic amine addition salt, pharmaceutical amino acid addition salt, etc. In some embodiments, the pharmaceutical metal salt comprises at least one of sodium salt, potassium salt, magnesium salt, calcium salt, aluminum salt, zinc salt, etc. In some embodiments, the pharmaceutical ammonium salt comprises ammonium salt, etc. In some embodiments, the pharmaceutical organic amine addition salt comprises alcohol amine salts, addition salt of morpholine, addition salt of piperidine, etc. In some embodiments, the pharmaceutical amino acid addition salt comprises at least one of Lysine salt, arginine salt, glycine salt, phenylalanine salt, aspartate salt, or glutamate salt, etc. The pharmaceutically acceptable salt is not to be limited hereto.

In present disclosure, the cosmetic active ingredients comprise at least one of a cosmetic monomer or cosmetic active ingredients having the same effect or different effects. For example, the effects comprise at least one of moisturizing, whitening, antioxidant, anti-wrinkle, anti-aging, and others.

In present disclosure, the additives are acceptable for a preparation of pharmaceutical formulations or cosmetic formulations, and the additives meet relevant pharmaceutical or cosmetic manufacturing regulations. The additives comprise, for example, at least one substance as follows: a diluent, a solvent, an excipient, an absorbent, a wetting agent, an adhesive, a disintegrant, an a lubricant, a solubilizer, an emulsifier, a suspending agent, a surfactant, a film-forming agent, a propellant, an antioxidant, a flavoring agent, a fragrance, a bactericide, or a preservative, etc.

Compared with existing techniques, the technical solution provided by the present disclosure has the following advantages.

In the transdermal absorption composition of the present disclosure, sponge spicules can be utilized with nanoparticles comprising one or more drugs or one or more cosmetic active ingredients synergistically. Such a combination use of the sponge spicules and the nanoparticles not only can overcome skin barrier of stratum corneum, but also it can lead to sustained or controlled drug release or sustained or controlled cosmetic active ingredient release within skin by being encapsulated in nanoparticles. Further, the combination use of the sponge spicules and the nanoparticles can improve the stability of drugs or cosmetic active ingredients by encapsulating them in nanoparticles and also can reduce toxic effects and side effects and reduce the risk of skin irritations by reducing the necessary dosage of drugs or cosmetic active ingredients. The combination use of the sponge spicules and the nanoparticles can provide an efficient and sustained skin delivery for a variety of drugs or cosmetic active ingredients with better skin safety.

BRIEF DESCRIPTION OF THE DRAWING

FIG. 2A illustrates a distribution profile of ANTS-Fucoidan in different skin layers. FIG. 2B illustrates a fluorescence image of ANTS-Fucoidan from a skin section of the control group. FIG. 2C illustrates a fluorescence image of ANTS-Fucoidan from a skin section of the group using the sponge spicules suspension. The scale of FIGS. 2B and 2C is 100 µm, and these components are the same across embodiments.

FIG. 3A illustrates a skin distribution profile of ANTS-Fucoidan in different skin layers. FIG. 3B illustrates a fluorescence image of ANTS-Fucoidan from a skin section of the control group. FIG. 3C illustrates a fluorescence image of ANTS-Fucoidan from a skin section of the group using the sponge spicules suspension and the flexible nanoliposomes.

FIG. 5A illustrates a distribution profile of FITC-Hyaluronic acid in different skin layers. FIG. 5B illustrates a fluorescence image of FITC-Hyaluronic acid from a skin section of the control group. FIG. 5C illustrates a fluorescence view of FITC-Hyaluronic acid from a skin section of the group using the sponge spicules suspension.

FIG. 6A illustrates a distribution profile of FITC-Hyaluronic acid in different skin layers. FIG. 6B illustrates a fluorescence image of FITC-Hyaluronic acid from a skin section of the control group. FIG. 6C illustrates a fluorescence image of FITC-Hyaluronic acid from a skin section of the group using the sponge spicules suspension and the conventional nanoliposomes.

FIG. 7A illustrates a distribution profile of FITC-Hyaluronic acid in different skin layers. FIG. 7B illustrates a fluorescence image of FITC-Hyaluronic acid from a skin section of the control group. FIG. 7C illustrates a fluorescence view of FITC-Hyaluronic acid from a skin section of the group using the sponge spicules suspension and the flexible nanoliposomes.

FIG. 9A illustrates a skin distribution profile of FITC-Hyaluronic acid in different skin layers. FIG. 9B illustrates a fluorescence image of FITC-Hyaluronic acid from a skin section of the group using the conventional nanoliposomes. FIG. 9C illustrates a fluorescence image of FITC-Hyaluronic acid from a skin section of the group using the sponge spicules suspension and the conventional nanoliposomes.

FIG. 10A illustrates a skin distribution profile of FITC-Hyaluronic acid in different skin layers. FIG. 10B illustrates a fluorescence image of FITC-Hyaluronic acid from a skin section of the group using the flexible nanoliposomes. FIG. 10C illustrates a fluorescence image of FITC-Hyaluronic acid from a skin section of the group using the sponge spicules suspension and the flexible nanoliposomes.

FIG. 11A illustrates a skin distribution profile of FITC-Hyaluronic acid in different skin layers. FIG. 11B illustrates a fluorescence image of FITC-Hyaluronic acid from a skin section of the group using the microneedles. FIG. 11C illustrates a fluorescence image of FITC-Hyaluronic acid from a skin section of the group using the sponge spicules suspension.

FIG. 12A illustrates a distribution profile of FITC-Hyaluronic acid in different skin layers. FIG. 12B illustrates a fluorescence image of FITC-Hyaluronic acid from a skin section of the group using the microneedles and the flexible nanoliposomes. FIG. 12C illustrates a fluorescence image of FITC-Hyaluronic acid from a skin section of the group using the sponge spicules suspension and the flexible nanoliposomes.

FIG. 14A illustrates the sponge spicules derived from *Haliclona* sp. with the high purity. FIG. 14B illustrates the sponge spicules derived from *Haliclona* sp. with the low purity. FIG. 14C illustrates the sponge spicules derived from Calcareous sponge. FIG. 14D illustrates the sponge spicules derived from *Tethya* sp. FIG. 14E illustrates the sponge spicules derived from Mycale sp.

FIG. 16A illustrates a distribution profile of FITC-Hyaluronic acid in different skin layers. FIG. 16B illustrates a fluorescence image of FITC-Hyaluronic acid from a skin section of the sponge spicules derived from *Tethya* sp. FIG. 16C illustrates a fluorescence image of FITC-Hyaluronic acid from a skin section of the sponge spicules derived from *Haliclona* sp. with a high purity.

FIGS. 17A-17C illustrate a comparative view of a skin absorption of FITC-Hyaluronic acid in different skin layers from a group using *Tethya* sp. and the flexible nanoliposomes and a group with using *Haliclona* sp. with a high purity and the flexible nanoliposomes in Embodiment 10. FIG. 17A illustrates a distribution profile of FITC-Hyaluronic acid in different skin layers. FIG. 17B illustrates a fluorescence image of FITC-Hyaluronic acid from a skin section of the group using *Tethya* sp. and the flexible nanoliposomes. FIG. 17C illustrates a fluorescence image of FITC-Hyaluronic acid from a skin section of the group using *Haliclona* sp. with a high purity and the flexible nanoliposomes.

FIGS. 18A-18L illustrate results of a skin irritation test by using the sponge spicules derived from *Haliclona* sp. with a high purity and the sponge spicules derived from *Haliclona* sp. with a low purity. FIG. 18A illustrates a picture of skin immediately (0 h) after being treated by the sponge spicules derived from the *Haliclona* sp. with a high purity. FIG. 18B illustrates a picture of skin immediately (0 h) after being treated by the sponge spicules derived from the *Haliclona* sp. with a low purity. FIG. 18C illustrates a picture of skin after being treated by the sponge spicules derived from the *Haliclona* sp. with a high purity for 24 h. FIG. 18D illustrates a picture of skin after being treated by the sponge spicules derived from the *Haliclona* sp. with a low purity for 24 h. FIG. 18E illustrates a picture of skin after being treated by the sponge spicules derived from the *Haliclona* sp. with a high purity for 48 h. FIG. 18F illustrates a picture of skin after being treated by the sponge spicules derived from the *Haliclona* sp. with a low purity for 48 h. FIG. 18G illustrates a picture of skin after being treated by the sponge spicules derived from the *Haliclona* sp. with a high purity for 96 h. FIG. 18H illustrates a picture of skin after being treated by the sponge spicules derived from the *Haliclona* sp. with a low purity for 96 h. FIG. 18I illustrates a picture of skin after being treated by the sponge spicules derived from the *Haliclona* sp. with a high purity for 168 h. FIG. 18J illustrates a picture of skin after being treated by the sponge spicules derived from the *Haliclona* sp. with a low purity for 168 h. FIG. 18K illustrates a picture of skin after being treated by the sponge spicules derived from the *Haliclona* sp. with a high purity for 240 h. FIG. 18L illustrates a picture of skin after being treated by the sponge spicules derived from the *Haliclona* sp. with a low purity for 240 h.

DETAILED DESCRIPTION OF THE EMBODIMENTS

Figure 1:
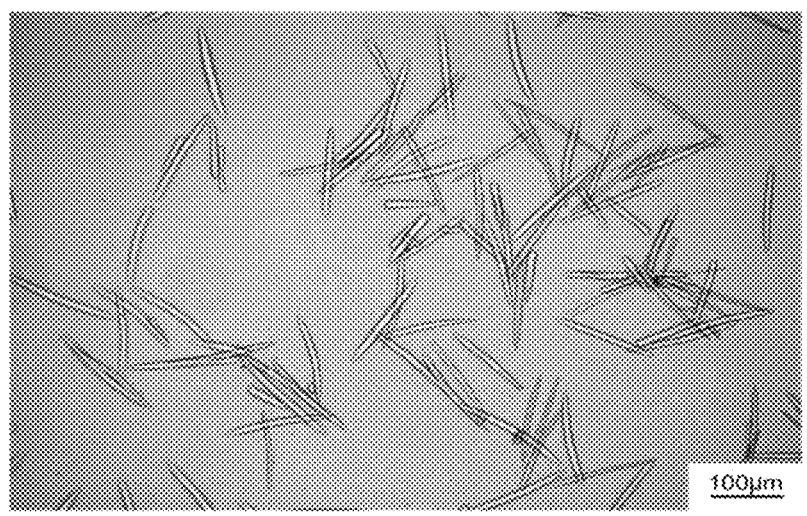
FIG. 1 illustrates appearances and structures of the sponge spicules under a microscope.

The present disclosure will be further described below with the combination of the accompanying drawings together with the embodiments.

Embodiment 1

(1) Pre-treatment of porcine skin: fresh porcine skin were obtained and the subcutaneous adipose tissue was removed. The porcine hair shaft was cut off to no more than 2 mm. The obtained skin was used immediately or stored at $-20°$ C.$--80°$ C. for use.

(2) Preparation of flexible nanoliposomes: a preset ratio of phospholipid 90 g (100 mg/mL), polyoxyethylene (20) oleoyl ether (100 mg/mL) as a surfactant, and methanol/chloroform at a 1:1 ratio was added into a round flask. A uniform film was formed on a bottom surface of the round flask by evaporating to dryness in a rotary evaporator. A solution of 1-5 mL comprising ANTS-Fucoidan was added into the round flask and a liposomal solution was obtained by film hydrating by flask shaking or ultrasonic dispersion, etc. A liposome extrusion device was used to squeeze the liposomal solution for 21 times, and it was finally transferred into an Eppendorf (EP) tube to obtain a solution of flexible nanoliposomes comprising ANTS-Fucoidan with a concentration of 1-100 mg/mL.

(3) Preparation of a sponge spicules suspension: a preset amount of PBS buffer with a molar concentration of 0.01-0.2M (mol/L) and a pH of 6.5-7.5, deionized water, physiological saline, double distilled water, or any solvent without any risk of skin irritation was mixed with the sponge spicules to obtain the sponge spicules suspension with a mass concentration of 0.01-100%.

(4) Skin penetration experiment in vitro: porcine skins with the same sizes were punched out with a round puncher. The porcine skins were mounted on a Franz diffusion cell. Transcutaneous electrical resistance of the porcine skins was measured in vitro to evaluate conductivity variation of the porcine skins before and after an application of the sponge spicules suspension. Before the application of the sponge spicules suspension, the porcine skins with the conductivity less than 10 µA were considered a good stratum corneum barrier of skin and can be used in following experiments. The conductivity of the porcine skins was increased to 40-150 µA after the application of the sponge spicules suspension, indicating that stratum corneum barrier of skin was disrupted by sponge spicules with varying degrees. A solution of 200 µL comprising ANTS-Fucoidan (an average molecular weight is 60 kDa) with a concentration of 1-100 mg/mL (a group using the sponge spicules suspension) or a solution comprising the flexible nanoliposomes encapsulating ANTS-Fucoidan with a concentration of 1-100 mg/mL (a group using the sponge spicule suspension and the flexible nanoliposomes) were applied on the skin evenly. The skin were incubated for 16 hours at 37° C. with stirring (600 r/min), and then the skin was taken out. The penetration enhancing effect of the sponge spicules on ANTS-Fucoidan was determined by both a quantitative method and a qualitative method.

Figures 2A, 2B, 2C:
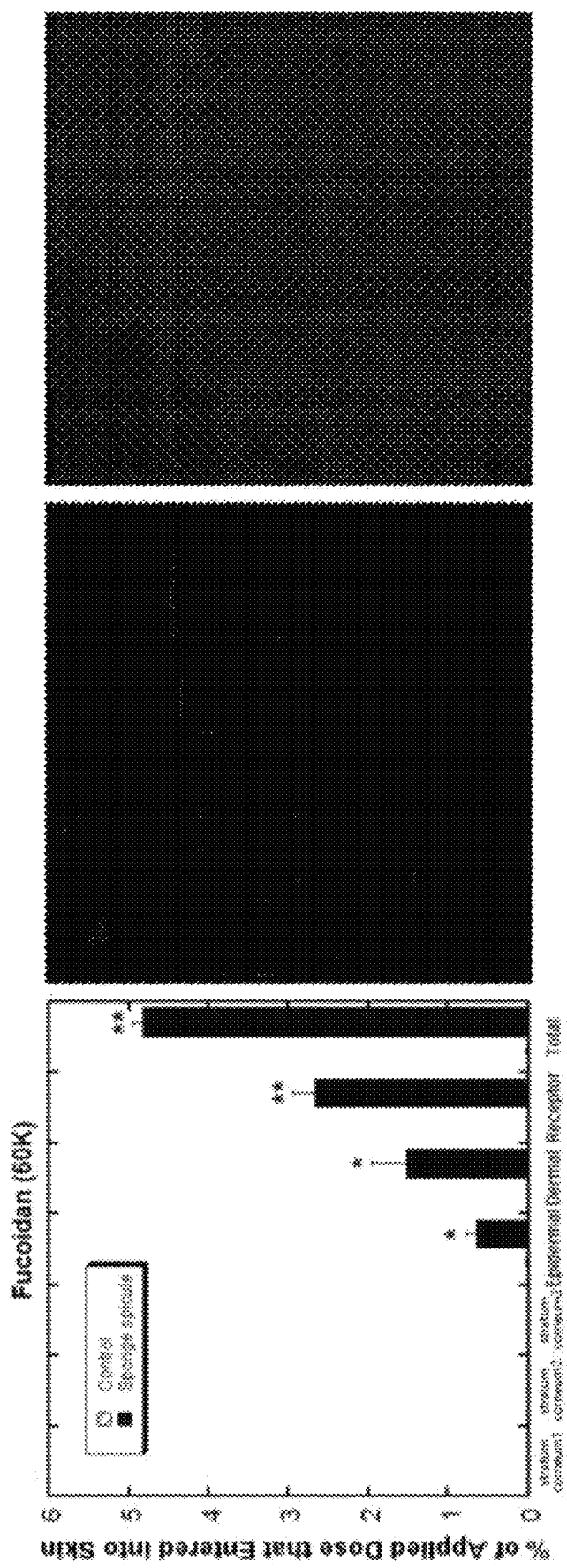
FIGS. 2A-2C illustrate a comparative view of skin penetration and deposition of ANTS-Fucoidan from a control group and from a group using a sponge spicules suspension in Embodiment 1. The concentration of ANTS-Fucoidan is 10 mg/mL, the concentration of the sponge spicules suspension is 100 mg/mL (equivalent to a mass concentration of 10%), a solvent involved is 100 µL of PBS 0.2 M (Mol/L) PBS (pH 7.4), and these components and conditions are the same across embodiments.
Figures 3A, 3B, 3C:
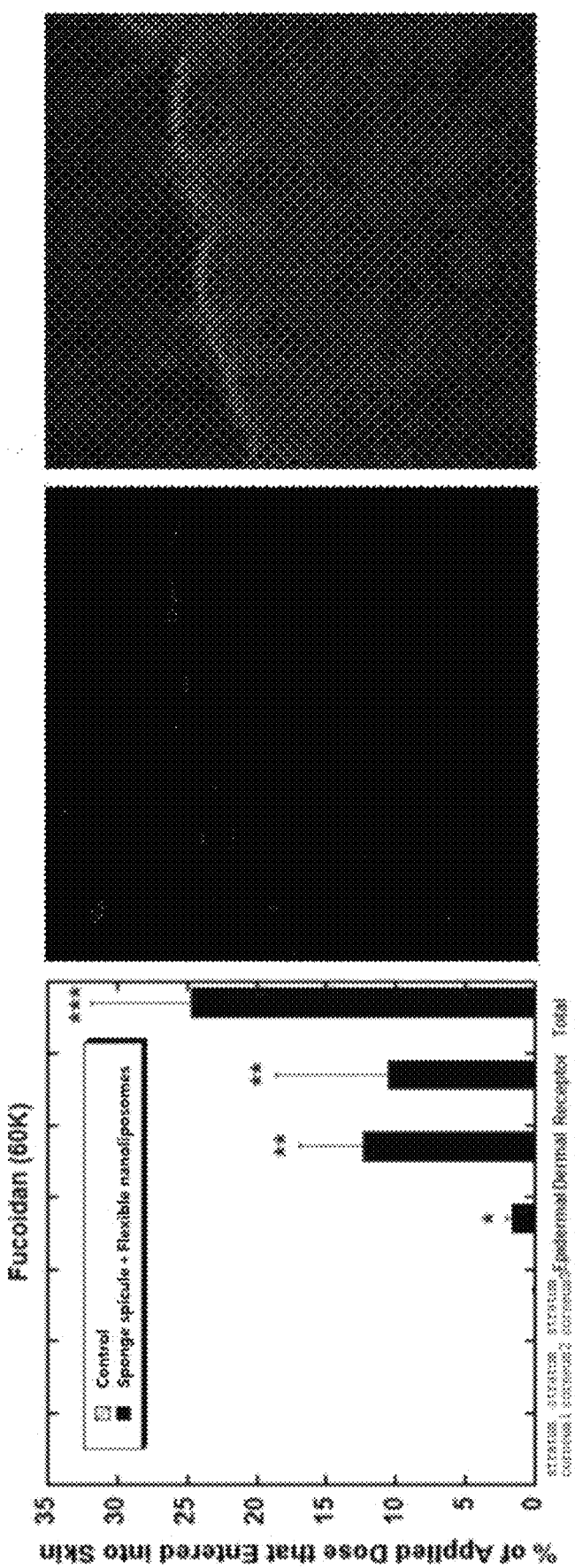
FIGS. 3A-3C illustrate a comparative view of skin penetration and deposition of ANTS-Fucoidan from the control group and a group using the sponge spicules suspension and flexible nanoliposomes in Embodiment 1. A concentration of phospholipid (90G) is 4%, a concentration of polyoxyethylene (20) oleyl ether (surfactant) is 1.2%, and these components are the same across embodiments.

(5) The quantitative method: ten layers of stratum corneum (SC) and active epidermis were separated from the skin by using a tape stripping method (Ten SC layers were collected according to the following scheme: SC 1=first strip, SC 2=second-fifth strips, and SC 3=sixth-tenth strips). After tape-stripping, the stratum corneum and the active epidermis was separated from dermis of the skin. The dermis was then cut into small pieces. A mixture (4 mL) of methanol and PBS (1:1, V/V) was used to extract ANTS-Fucoidan from separated skin layers at room temperature (i.e., 20-25° C.) with a speed of 200 r/min for 8-24 hours. The concentration of ANTS-Fucoidan in the stratum corneum, the active epidermis, the dermis, and receptor phase were determined by a full-wavelength microplate reader at the detection wavelength of ANTS (excitation wavelength: 350 nm, and emission wavelength: 520 nm). Referring to FIGS. 2A-2C, as a result, compared with the control group, a total skin absorption in skin layers of ANTS-Fucoidan from the group using the sponge spicules suspension increased from 0.01% to 4.83%. Referring to FIGS. 3A-3C, a total skin absorption of ANTS-Fucoidan in skin layers from the group using the sponge spicules suspension and the flexible nanoliposomes greatly increased to 24.76%.

Figure 4:
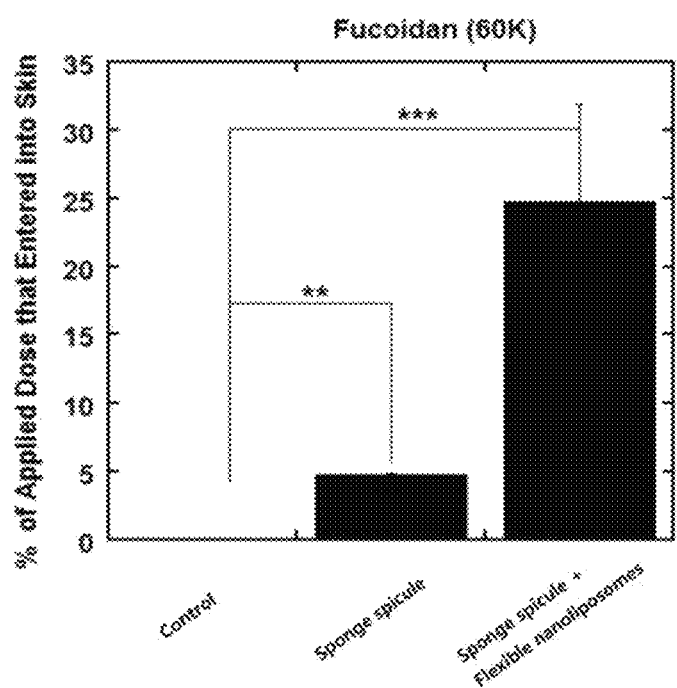
FIG. 4 illustrates a comparative view of a total skin absorption of ANTS-Fucoidan from the control group, the group using the sponge spicules suspension, and the group using the sponge spicules suspension and the flexible nanoliposomes in Embodiment 1.

(6) The qualitative method: porcine skin sections with the same sizes were punched out by a round puncher with a diameter of 5 mm and then immediately frozen in optimal cutting temperature (OCT) compound and sectioned at a thickness of 20 µm to obtain skin section slices. The skin section slices were sealed by neutral resin. Referring to FIGS. 2-4, skin distributions of ANTS-Fucoidan in different skin layers from the control group, the group using the sponge spicules suspension, and the group using the sponge spicules suspension and the flexible nanoliposomes were observed by a confocal microscope.

FIG. 1 illustrates appearances and structures of the sponge spicules under a microscope. FIGS. 2A-2C illustrate comparative results of skin absorption of ANTS-Fucoidan from the control group and the group using the sponge spicules suspension in Embodiment 1 (comprising a distribution profile of ANTS-Fucoidan in the skin layers and a fluorescence image of ANTS-Fucoidan from the skin section slices). FIGS. 3A-3C illustrate comparative results of skin absorption of ANTS-Fucoidan from the control group and the group using the sponge spicules suspension and the flexible nanoliposomes in Embodiment 1. FIG. 4 illustrates a comparative view of a total skin absorption of ANTS-Fucoidan from the control group, the group using the sponge spicules suspension, and the group using the sponge spicules suspension and the flexible nanoliposomes in Embodiment 1.

Embodiment 2

(1) Pre-treatment of a porcine skin: the same as that in Embodiment 1.

(2) Preparation of conventional nanoliposomes: a preset ratio of phospholipid 90 g (100 mg/mL) and methanol/ chloroform at a ratio of 1:1 was added into a round flask. A uniform film was formed on a bottom surface of the round flask by evaporating to dryness in a rotary evaporator. A solution of 1-5 mL comprising FITC-Hyaluronic acid was added into the round flask and a liposomal solution was obtained by film hydrating by flask shaking or ultrasonic dispersion, etc. A liposome extrusion device was used to squeeze the liposomal solution for 21 times, and it was finally transferred into an Eppendorf (EP) tube to obtain a solution of conventional nanoliposomes comprising FITC-Hyaluronic acid with a concentration of 1-100 mg/mL.

(3) Preparation of flexible nanoliposomes: similar with that in Embodiment 1.

(4) Preparation of a sponge spicules suspension: the same as that in Embodiment 1.

(5) Skin penetration experiment in vitro: similar with Embodiment 1, a control group (a solution comprising FITC-Hyaluronic acid), a conventional nanoliposomes group (a solution comprising conventional nanoliposomes and FITC-Hyaluronic acid), and a flexible nanoliposomes group (a solution comprising flexible nanoliposomes and FITC-Hyaluronic acid). The solution of 150 μL comprising FITC-Hyaluronic acid (an average molecular weight of 250 KDa) with a concentration of 1-100 mg/mL (a group using the sponge spicules suspension), the solution comprising the conventional nanoliposomes and FITC-Hyaluronic acid with a concentration of 1-100 mg/mL (a group using the sponge spicules suspension and the conventional nanoliposomes), or the solution comprising the flexible nanoliposomes and FITC-Hyaluronic acid with a concentration of 1-100 mg/mL (a group using the sponge spicules suspension and the flexible nanoliposomes) were applied on the skin evenly. The skins were incubated for 16 hours at 37° C. with stirring (600 r/min), and the skins ware taken out. The penetration enhancing effect of the sponge spicules suspension on skin penetration of ANTS-Fucoidan was determined by both a quantitative method and a qualitative method.

(6) The quantitative method: similar with that in Embodiment 1. Skin deposition of FITC-Hyaluronic acid in stratum corneum, active epidermis, dermis, and receptor phase were determined by a full-wavelength microplate reader at the detection wavelength of FITC (excitation wavelength: 490 nm, and emission wavelength: 530 nm). Referring to FIG. 5, as a result, compared with the control group, a total skin absorption of FITC-Hyaluronic acid in skin layers from the group using the sponge spicules suspension increased from 1.2% to 6.92%. Referring to FIG. 6, a total skin absorption of FITC-Hyaluronic acid in skin layers from the group using the sponge spicules suspension and the conventional nanoliposomes group increased to 9.01%. Referring to FIG. 7, a total skin absorption of FITC-Hyaluronic acid in skin layers from the group using the sponge spicules suspension and the flexible nanoliposomes greatly increased to 37.89%.

Figures 7A, 7B, 7C:
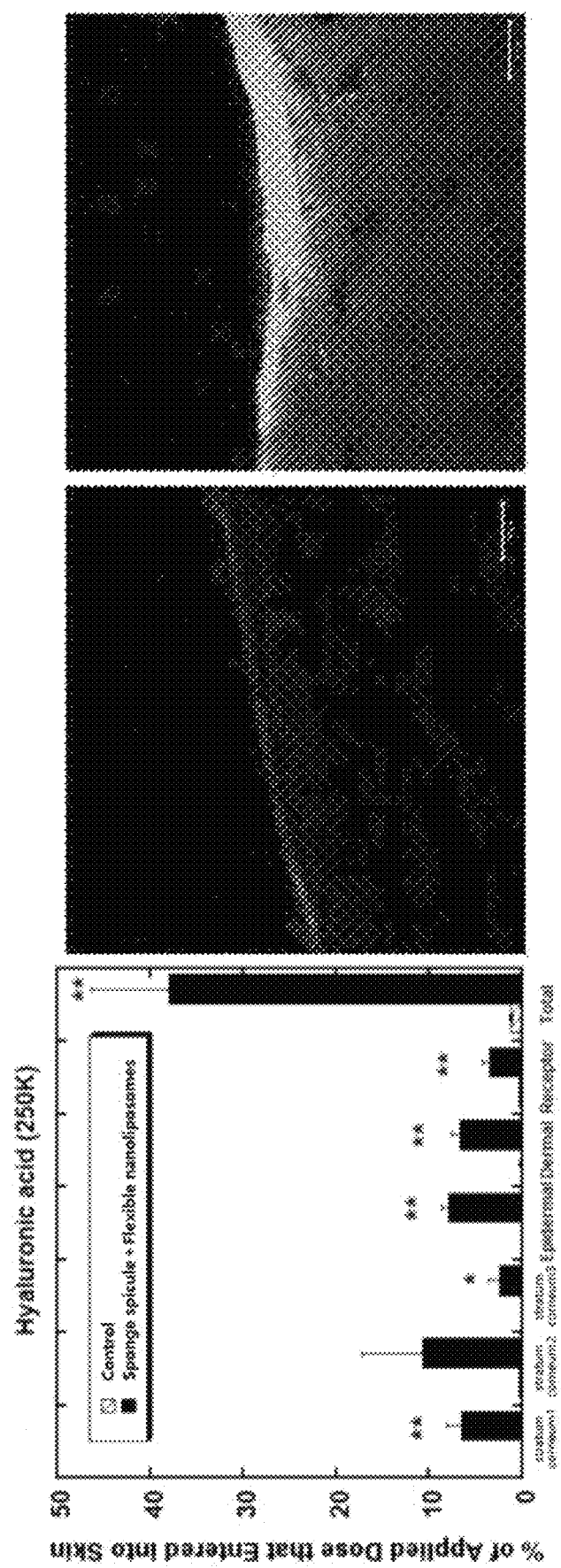
FIGS. 7A-7C illustrate a comparative view of skin penetration and deposition of FITC-Hyaluronic acid from the control group and the group using the sponge spicules suspension and the flexible nanoliposomes in Embodiment 2. The concentration of phospholipid (90G) is 4%, and the concentration of polyoxyethylene (20) oleyl ether (surfactant) is 1.2%, and these components are the same across embodiments.
Figure 8:
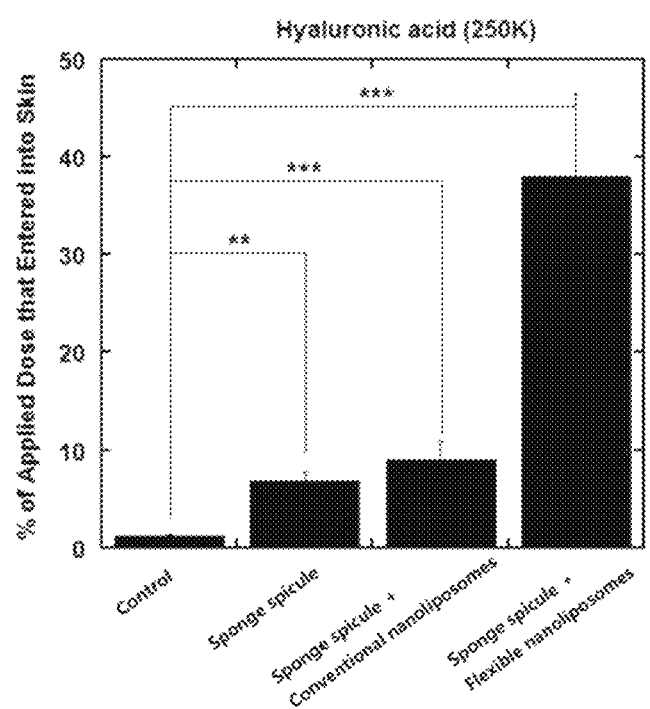
FIG. 8 illustrates a comparative view of a total skin absorption of FITC-Hyaluronic acid from the control group, the group using the sponge spicules suspension, the group using the sponge spicules suspension and the conventional nanoliposomes, and the group using the sponge spicules suspension and the flexible nanoliposomes in Embodiment 2.

(7) The qualitative method: similar with that in Embodiment 1. Referring to FIGS. 6-8, skin distributions of FITC-Hyaluronic acid in different skin layers from the control group, the group using the sponge spicules suspension, the group using the sponge spicules suspension and the conventional nanoliposomes, and the group using the sponge spicules suspension and the flexible nanoliposomes were observed by a confocal microscope.

Figure 5C:
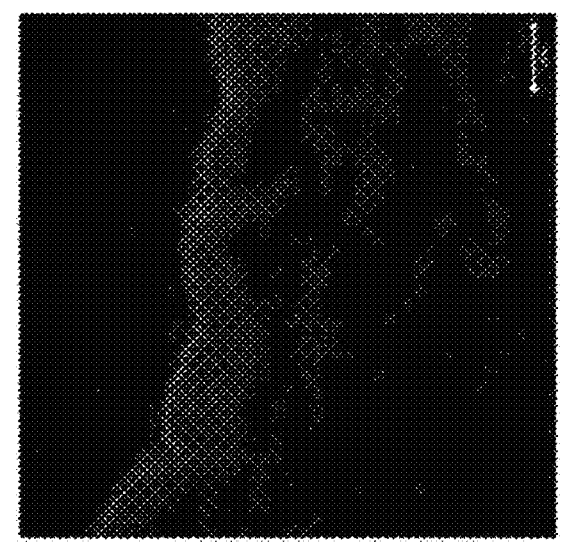
FIGS. 5A-5C illustrate a comparative view of skin penetration and deposition of FITC-Hyaluronic acid from a control group and a group using the sponge spicules suspension in Embodiment 2. A concentration of FITC-Hyaluronic acid is 1 mg/mL, the concentration of the sponge spicules suspension is 100 mg/mL (equivalent to a mass concentration of 10%), a solvent involved is 100 µL of PBS (0.2 M, pH 7.4), and these components and conditions are the same across embodiments.
Figure 5B:
Figure 5A:
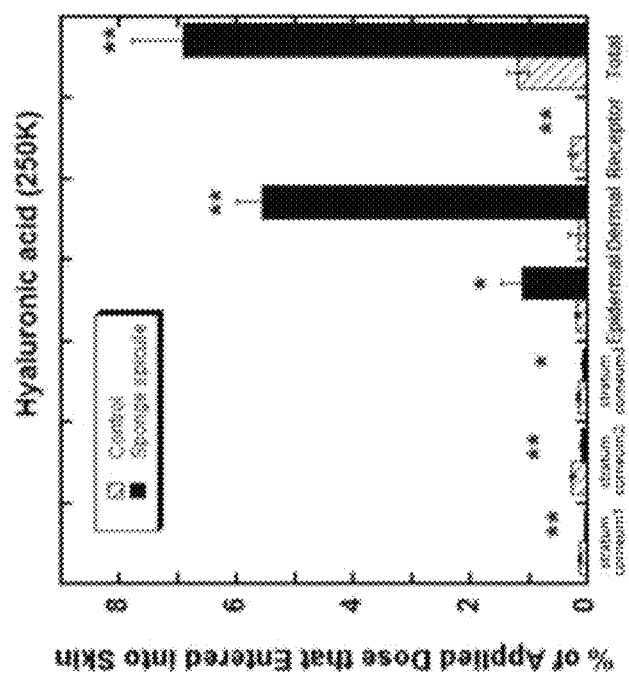
Figure 6C:
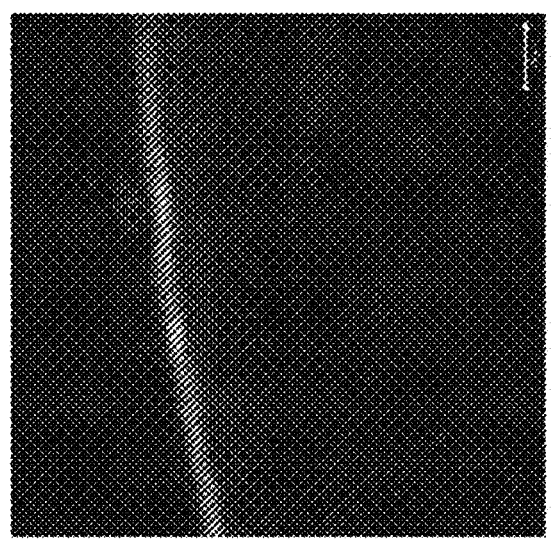
FIGS. 6A-6C illustrate a comparative view of skin penetration and deposition of FITC-Hyaluronic acid from the control group and a group using the sponge spicules suspension and the conventional nanoliposomes in Embodiment 2. The concentration of phospholipid (90G) is 4%, and these components are the same across embodiments.
Figure 6B:
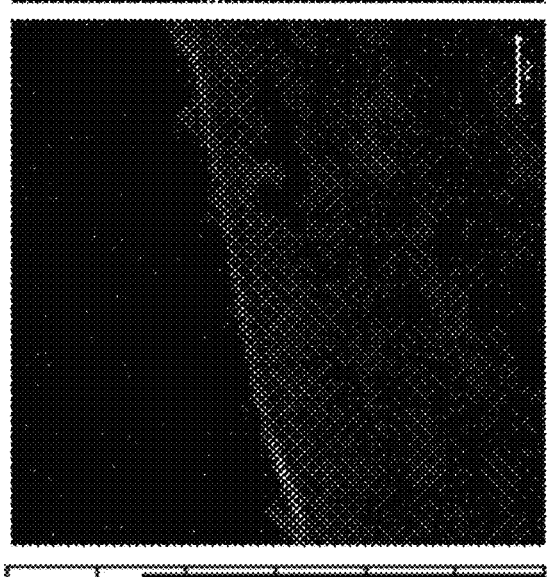
Figure 6A:
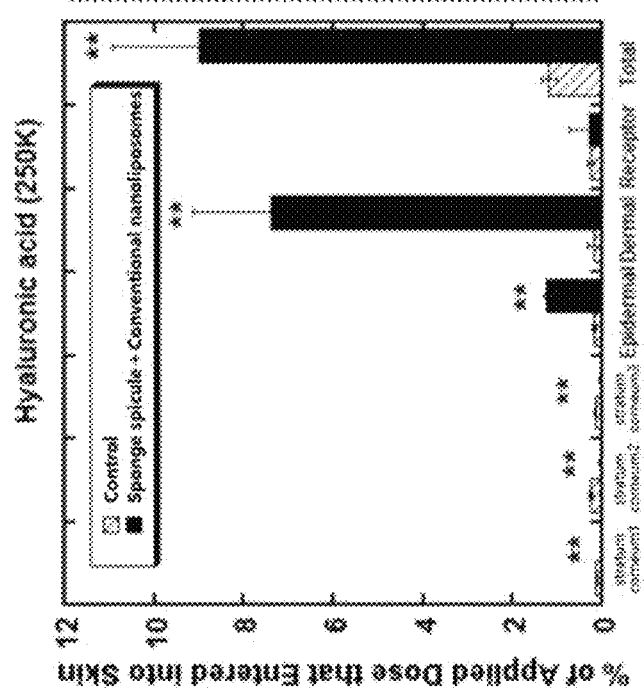
Figures 9A, 9B, 9C:
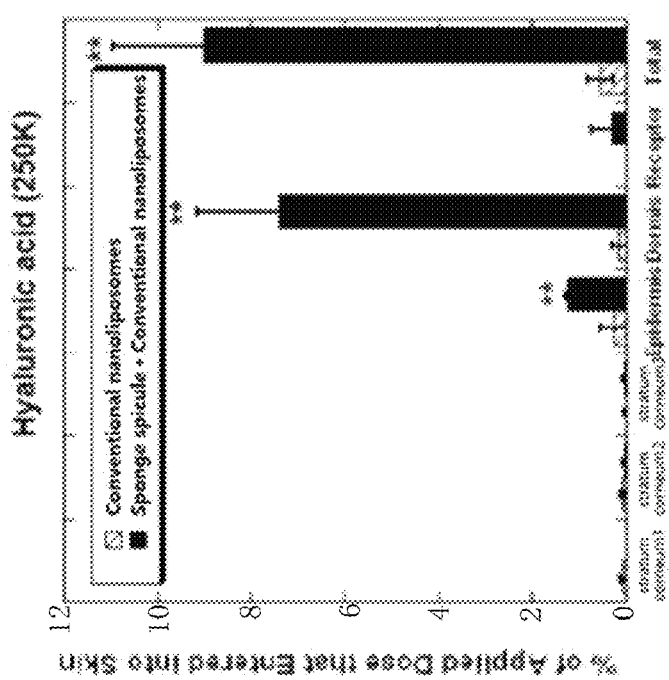
FIGS. 9A-9C illustrate a comparative view of a total skin absorption of FITC-Hyaluronic acid from a group using the conventional nanoliposomes and the group using the sponge spicules suspension and the conventional nanoliposomes in Embodiment 2.
Figure 10C:
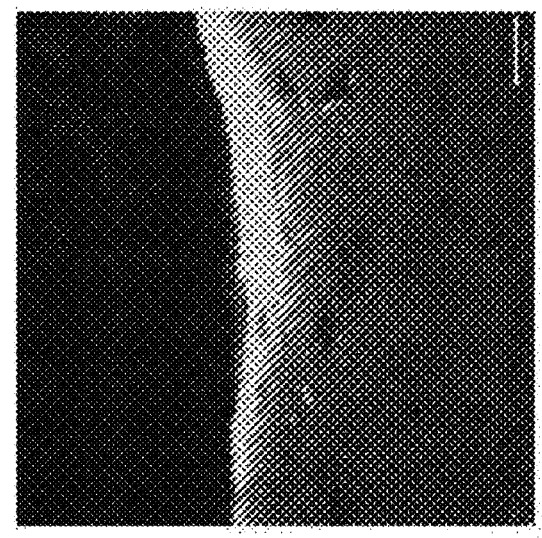
FIGS. 10A-10C illustrate a comparative view of a total skin absorption of FITC-Hyaluronic acid from a group using the flexible nanoliposomes and a group using the sponge spicules suspension and the flexible nanoliposomes in Embodiment 2.
Figure 10B:
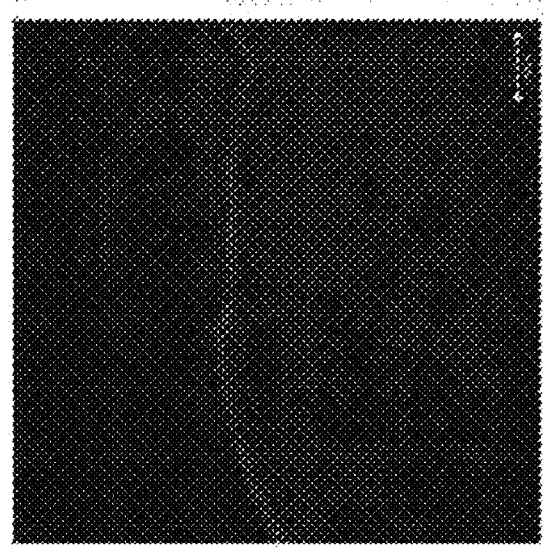
Figure 10A:
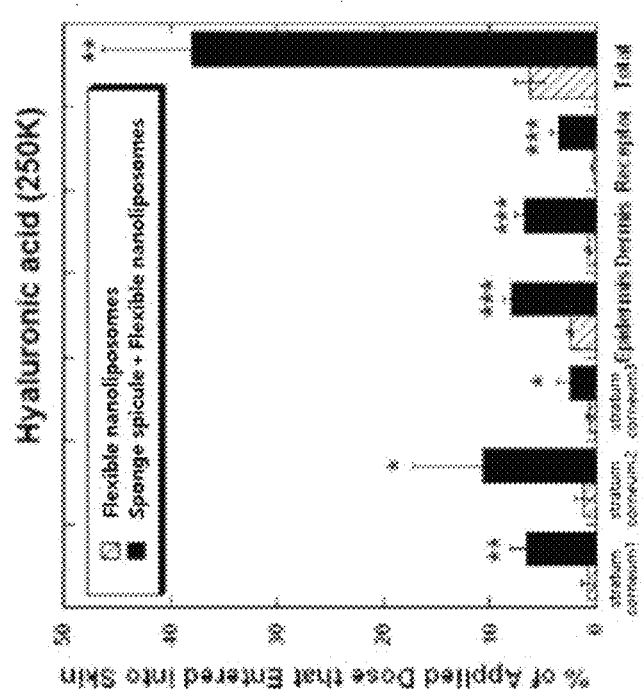

FIGS. 5A-5C illustrate comparative results of skin penetration of FITC-Hyaluronic acid from the control group and the group using the sponge spicules suspension in Embodiment 2. FIGS. 6A-6C illustrate comparative results of skin penetration of FITC-Hyaluronic acid from the control group and the group using the sponge spicules suspension and the conventional nanoliposomes in Embodiment 2. FIGS. 7A-7C illustrate comparative results of skin penetration of FITC-Hyaluronic acid from the control group and the group using the sponge spicules suspension and the flexible nanoliposomes in Embodiment 2. FIG. 8 illustrates a comparative view of a total skin absorption of FITC-Hyaluronic acid from the control group, the group using the sponge spicules suspension, the group using the sponge spicules suspension and the conventional nanoliposomes, and the group using the sponge spicules suspension and the flexible nanoliposomes in Embodiment 2. FIGS. 9A-9C illustrate comparative results of skin penetration of FITC-Hyaluronic acid from the group using of the sponge spicules suspension and the conventional nanoliposomes, and a group using the conventional nanoliposomes in Embodiment 2. FIGS. 10A-10C illustrate comparative results of skin penetration of FITC-Hyaluronic acid from the group using the sponge spicules suspension and the flexible nanoliposomes, and a group using the flexible nanoliposomes in Embodiment 2.

From the results, the skin penetration enhancing effect of the group using the sponge spicules suspension and the conventional nanoliposomes is better than those of the control group, the group using the sponge spicules suspension, and the group using the conventional nanoliposomes, which indicates that a combination use of the sponge spicules and the conventional nanoliposomes had synergistic effect on improving skin drug delivery and therefore significantly increased the skin absorption of drug. In addition, the group using the sponge spicules and the flexible nanoliposomes show much better skin penetration enhancing effect than the control group, the group using the sponge spicules suspension, and the group using the flexible nanoliposomes, which indicates that a combination use of the sponge spicules and flexible nanoliposomes had synergistic effect on improving skin drug delivery and therefore significantly increased the skin absorption of drug. Moreover, the synergy effect induced by the combination use of the sponge spicules and the flexible nanoliposomes is much better than that induced by the combination use of the sponge spicules and the conventional nanoliposomes.

Figures 11A, 11B, 11C:
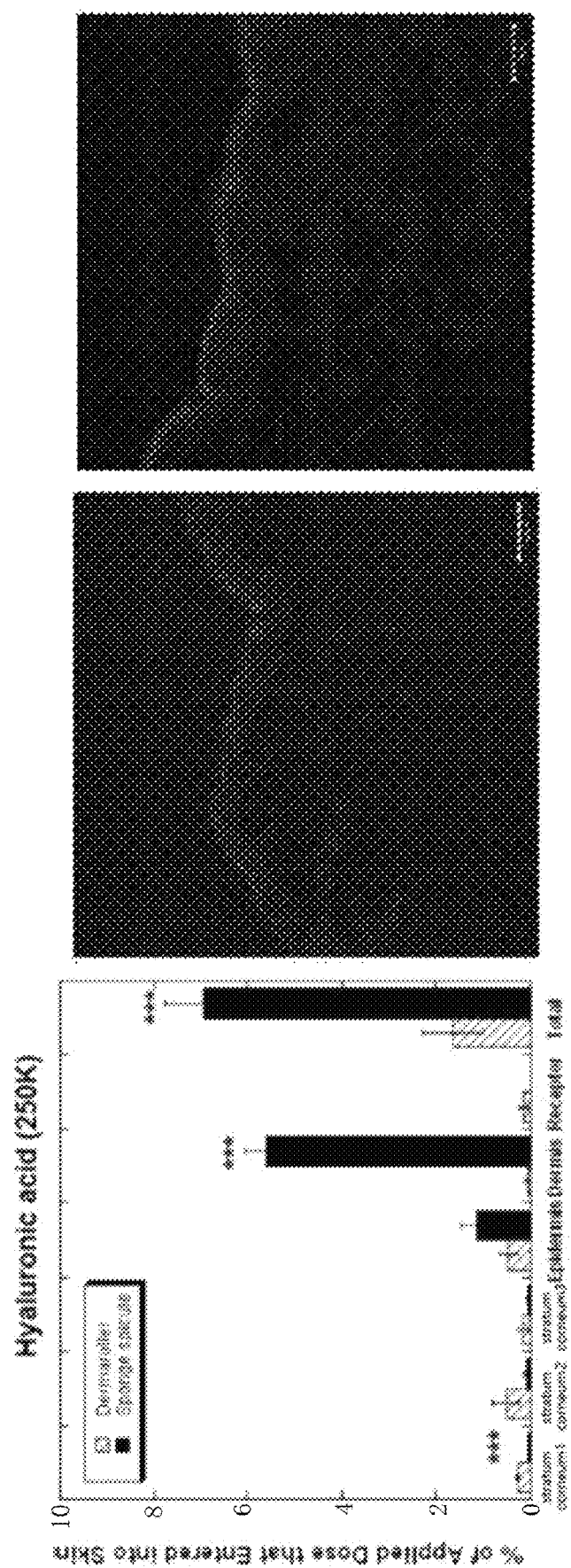
FIGS. 11A-11C illustrate a comparative view of a total skin absorption of FITC-Hyaluronic acid from a group using microneedles and a group using the sponge spicules suspension in Embodiment 2.
Figure 12A:
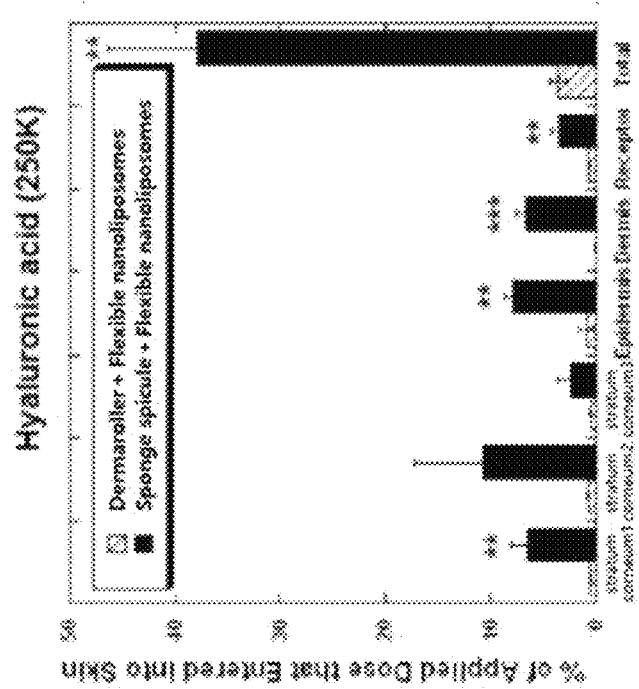
FIGS. 12A-12C illustrate a comparative view of a total skin absorption of FITC-Hyaluronic acid from a group using microneedles and the flexible nanoliposomes and a group using the sponge spicules suspension and the flexible nanoliposomes in Embodiment 2.
Figure 12B:
Figure 12C:
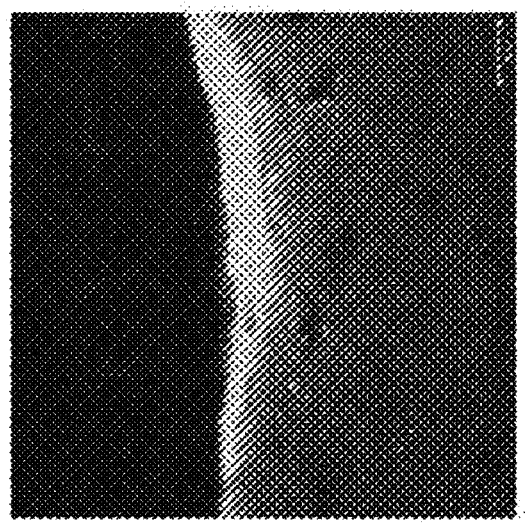

Further, the sponge spicules (i.e., the group using the sponge spicules suspension or the group using the sponge spicules suspension and the flexible nanoliposomes) of the present disclosure are compared with a traditional microneedle (Dermaroller). FIGS. 11A-11C illustrate comparative results of skin penetration of FITC-Hyaluronic acid from a group using microneedles and the group using the sponge spicules suspension in Embodiment 2. FIGS. 12A-12C illustrate comparative results of skin penetration of FITC-Hyaluronic acid from a group using the microneedles and the flexible nanoliposomes and the group using the sponge spicules suspension and the flexible nanoliposomes in Embodiment 2. As illustrated, skin penetration enhancing effects of the sponge spicules (i.e., the group using the sponge spicules suspension or the group using the sponge spicules suspension and the flexible nanoliposomes) are significantly better than that of the microneedles (i.e., the group using the microneedles or the group using the microneedles and the flexible nanoliposomes).

Figure 13:
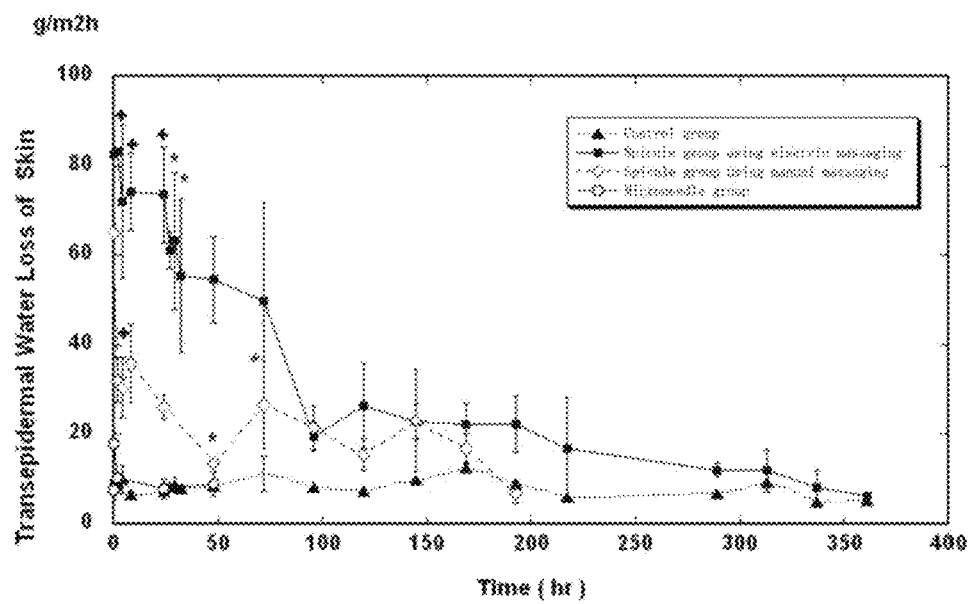
FIG. 13 illustrates a comparative view of a transepidermal water loss over 360 hours of a control group, a group using the microneedles, a group using sponge spicules suspension and massaging by hand, and a group using sponge spicules suspension and massaging by an electric massager in Embodiment 2.

FIG. 13 illustrates comparative results of transepidermal water loss over 360 hours of the control group, the group using the microneedles, the group using the sponge spicules suspension with massaging by hand, and the group with the sponge spicules suspension with massaging by an electric massager in Embodiment 2. Compared with the microneedles, the sponge spicules can retain in the stratum corneum of the skin for a long time and create a plenty of long-lasting microchannels, thereby increasing the skin absorption of biomacromolecular drugs or cosmetic active ingredients.

Embodiment 3

(1) Pre-treatment of a porcine skin: the same as Embodiment 1.

(2) Preparation of solid lipid nanoparticles: prepared according to existing techniques.

(3) Preparation of the sponge spicules suspension: the same as Embodiment 1.

(4) Skin penetration experiment in vitro: prepared according to Embodiment 1. As a result, the group using the sponge spicules suspension and the solid lipid nanoparticles has a significant skin penetrating enhancing effect compared to the other groups (i.e., the control group and the group using the sponge spicules suspension).

Embodiment 4

(1) Pre-treatment of a porcine skin: the same as Embodiment 1.

(2) Preparation of nanocapsules: prepared according to existing techniques.

(3) Preparation of the sponge spicules suspension: the same as Embodiment 1.

(4) Skin penetration experiment in vitro: prepared according to Embodiment 1. As a result, a group using the sponge spicules suspension and the nanocapsules has a significant skin penetrating enhancing effect compared to the other groups (i.e., the control group and the group using the sponge spicules suspension).

Embodiment 5

(1) Pre-treatment of a porcine skin: the same as Embodiment 1.

(2) Preparation of nanospheres: prepared according to existing techniques.

(3) Preparation of the sponge spicules suspension: the same as Embodiment 1.

(4) Skin penetration experiment in vitro: prepared according to Embodiment 1. As a result, a group using the sponge spicules suspension and the nanospheres has a significant skin penetrating enhancing effect relative to the other groups (i.e., the control group and the group using the sponge spicules suspension).

Embodiment 6

(1) Pre-treatment of a porcine skin: the same as Embodiment 1.

(2) Preparation of polymer micelle: prepared according to existing techniques.

(3) Preparation of the sponge spicules suspension: the same as Embodiment 1.

(4) Skin penetration experiment in vitro: prepared according to Embodiment 1. As a result, a group using the sponge spicules suspension and the polymer micelle has a significant skin penetrating enhancing effect relative to the other groups (i.e., the control group and the group using the sponge spicules suspension).

Embodiment 7

(1) Pre-treatment of porcine skin: the same as Embodiment 1.

(2) Preparation of nanosuspensions: prepared according to existing techniques.

(3) Preparation of the sponge spicules suspension: the same as Embodiment 1.

(4) Skin penetration experiment in vitro: prepared according to Embodiment 1. As a result, a group using the sponge spicules suspension and the nanosuspensions has a significant skin penetrating enhancing effect relative to the other groups (i.e., the control group and the group using the sponge spicules suspension).

Embodiment 8

(1) Pre-treatment of a porcine skin: the same as Embodiment 1.

(2) Preparation of ethosomes: prepared according to existing techniques.

(3) Preparation of the sponge spicules suspension: the same as Embodiment 1.

(4) Skin penetration experiment in vitro: prepared according to Embodiment 1. As a result, a group using the sponge spicules suspension and the ethosomes has a significant skin penetrating enhancing effect relative to the other groups (i.e., the control group and the group using the sponge spicules suspension).

Embodiment 9

(1) Pre-treatment of a porcine skin: the same as Embodiment 1.

(2) Preparation of nano-sized particles: prepared according to existing techniques.

(3) Preparation of the sponge spicules suspension: the same as Embodiment 1.

(4) Skin penetration experiment in vitro: prepared according to Embodiment 1. As a result, a group of the sponge spicules suspension and the nano-sized particles has a significant skin penetrating enhancing effect relative to the other groups (i.e., the control group and the group using the sponge spicules suspension).

Embodiment 10

Figures 14A, 14B:
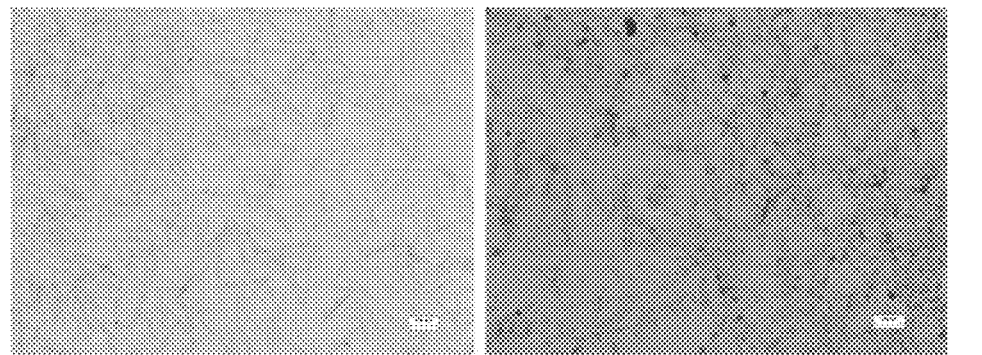
FIGS. 14A-14E illustrate a comparative view of morphologies of sponge spicules derived from *Haliclona* sp. with a high purity, sponge spicules derived from *Haliclona* sp. with a low purity, sponge spicules derived from Calcareous sponge, sponge spicules derived from *Tethya* sp., and sponge spicules derived from Mycale sp. The scale of FIGS. 14A-14E is 100 µm.
Figures 14C, 14D, 14E:
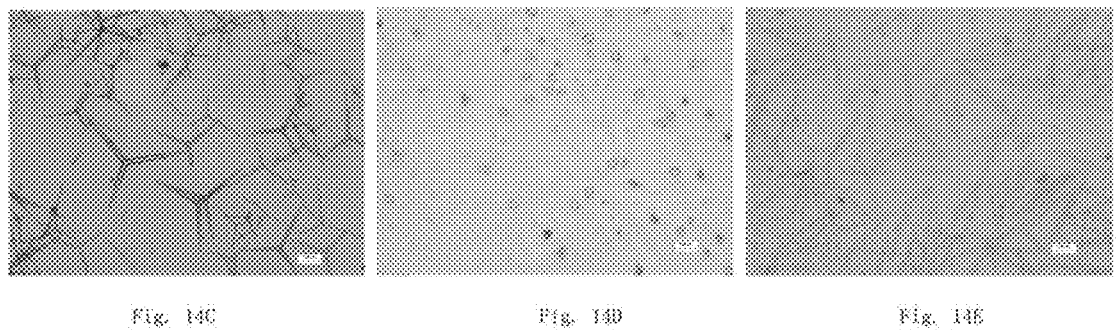

FIGS. 14A-14E illustrate a morphological comparison view of sponge spicules derived from *Haliclona* sp. with a high purity, sponge spicules derived from *Haliclona* sp. with a low purity, sponge spicules derived from Calcareous sponge, sponge spicules derived from *Tethya* sp., and sponge spicules derived from Mycale sp. FIG. 14A illustrates a morphology of oxea spicules derived from *Haliclona* sp. with a high purity. FIG. 14B illustrates a morphology of oxea spicules derived from *Haliclona* sp. with a low purity. The sponge spicules derived from *Haliclona* sp. with high purity have more uniform shapes, more integrated structures, and less impurities. FIG. 14C illustrates a morphology of triactine spicules derived from Calcareous sponge. FIG. 14D illustrates a morphology of acanthostyle spicules derived from *Tethya* sp. FIG. 14E illustrates a morphology of style spicules derived from Mycale sp.

Figure 15:
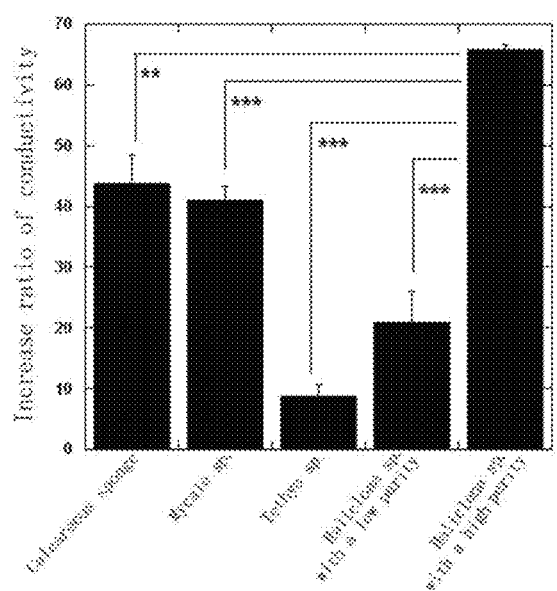
FIG. 15 illustrates a comparative view of effects on skin barrier of different species and different morphologies of the sponge spicules.

Referring to the skin penetration experiment in vitro of Embodiment 1 (step 4 of Embodiment 1), penetration-enhancing effects of the sponge spicules derived from different species and with different morphology were investigated. The results are shown in FIG. 15. While skin were treated with different sponge spicules derived from different species but at the same concentration, the sponge spicules derived from *Haliclona* sp. with a high purity (a purity of 99.5%) led to a much significantly higher enhancement ratio of skin conductivity than the sponge spicules derived from Calcareous sponge (a purity of 95.1%), the sponge spicules derived from *Tethya* sp. (a purity of 93.2%), the sponge spicules derived from Mycale sp. (a purity of 96.7%), and the sponge spicules derived from *Haliclona* sp. with a low purity (a purity of 69.9%), which indicates that penetration-enhancing effect of the sponge spicules derived from *Haliclona* sp. with a high purity are much more efficient than those of the sponge spicules derived from Calcareous sponge, the sponge spicules derived from *Tethya* sp., the sponge spicules derived from Mycale sp., and the sponge spicules derived from *Haliclona* sp. with a low purity.

Figure 16C:
FIGS. 16A-16C illustrate a comparative view of a skin absorption of FITC-Hyaluronic acid in different skin layers after applied with the sponge spicules derived from *Tethya* sp. and the sponge spicules derived from *Haliclona* sp. with a high purity in Embodiment 10.
Figure 16B:
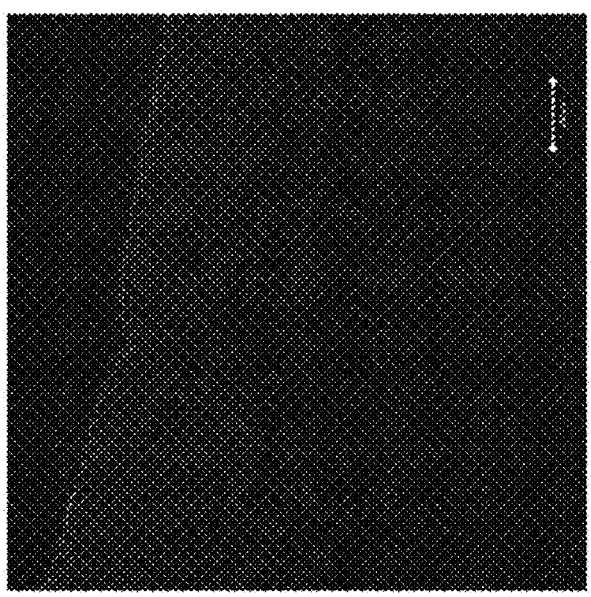
Figure 16A:
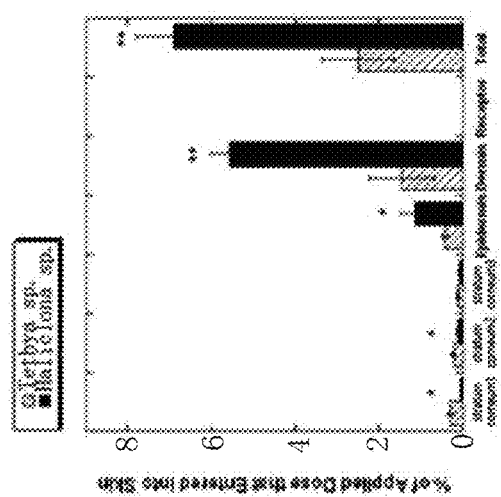
Figure 19:
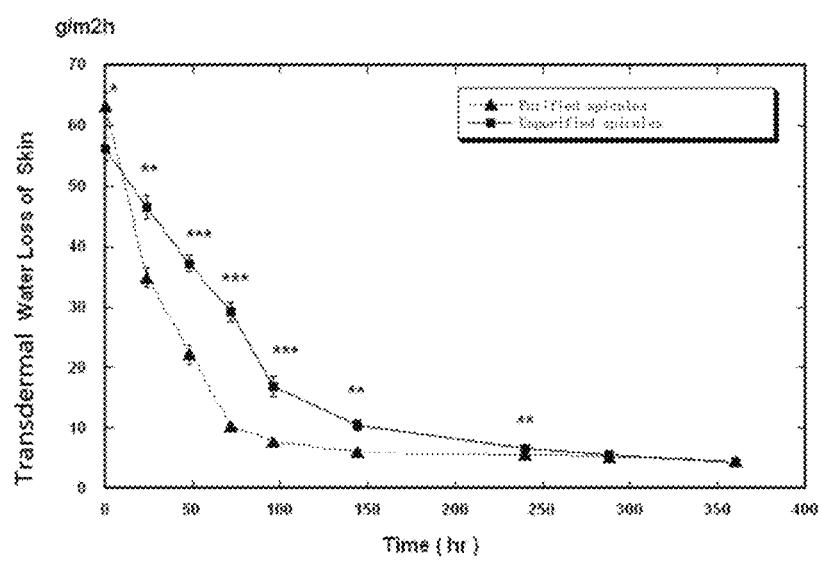
FIG. 19 illustrates a comparative view of a time-recovery curve of a barrier function of the skin after the skin being treated by the sponge spicules derived from *Haliclona* sp. with a high purity (purified spicules) and the sponge spicules derived from *Haliclona* sp. with a low purity (unpurified spicules).

Referring to the method of Embodiment 2, the skin penetration and deposition of FITC-Hyaluronic acid induced by a group using the sponge spicules derived from *Tethya* sp. and induced by a group using the sponge spicules derived from *Haliclona* sp. with a high purity were compared. As shown in FIGS. 16A-16C, the sponge spicules derived from *Haliclona* sp. with a high purity resulted in a better penetration-enhancing effect.

Referring to the method of Embodiment 2, the skin penetration and deposition of FITC-Hyaluronic acid induced by the group using the sponge spicules derived from *Tethya* sp. and the flexible nanoliposomes and induced by the group using the sponge spicules derived from *Haliclona* sp. with a high purity and the flexible nanoliposomes were compared. As shown in FIGS. 17A-17C, a total skin absorption of FITC-Hyaluronic acid from the group using the sponge spicules derived from *Haliclona* sp. with the high purity and the flexible nanoliposomes was 37.89%, while a total skin absorption of FITC-Hyaluronic acid from the group using the sponge spicules derived from *Tethya* sp. and the flexible nanoliposomes group is 4.76%, which indicates that the group using the sponge spicules derived from *Haliclona* sp. with a high purity and the flexible nanoliposomes group has a much better penetration-enhancing effect.

Embodiment 11

Sponge spicules derived from *Haliclona* sp. with a high purity and sponge spicules derived from *Haliclona* sp. with a low purity were used in skin irritation experiments.

Experimental method: the hair shaft of guinea pig was shaved. A suspension of 100 µL comprising 100 mg/mL (equivalent to 10% mass concentration) sponge spicules derived from *Haliclona* sp. with a high purity (purity of 99.5%) and a suspension of 100 µL comprising 100 mg/mL (equivalent to 10% mass concentration) sponge spicules derived from *Haliclona* sp with a low purity (purity of 69.9%) were applied on two symmetrical sides of the back of the guinea pig with massaging for two minutes. After massaging, transepidermal water loss of the treated skin area were measured and recorded by photos at $24^{th}$ hour, $48^{th}$ hour, $96^{th}$ hour, $168^{th}$ hour, and $240^{th}$ hour.

The results are shown in FIGS. 18A-18L and 19. The guinea pig skin treated by the sponge spicules derived from *Haliclona* sp. with a high purity were basically recovered after 96 hours and without infection. In contrast, the guinea pig skin treated by the sponge spicules derived from *Haliclona* sp. with a low purity appeared to be red with the signs of infection. Further, the speed of skin recovery was slowed down, and the wounds were basically recovered after 168 hours. Considering skin immunity, the faster skin recovers, the lower the risk to be infected by external pathogens. When treated with the sponge spicules derived from *Haliclona* sp. with a high purity, skin recovered with a faster speed, indicating that the sponge spicules derived from *Haliclona* sp. with a high purity leads to a better safety of its application.

Embodiment 12

Flexible nanoliposomes were extruded through a membrane with a pore size of 200 nm, an average particle size (i.e., particle sizes) of the flexible nanoliposomes was 168.13 nm±2.99 nm. Flexible nanoliposomes were extruded through a membrane with a pore size of 100 nm, an average particle size (i.e., particle sizes) of the flexible nanoliposomes 130.57 nm±0.65 nm.

Test method: 1 mL of different testing samples respectively comprising pure water, conventional nanoliposomes, or the flexible nanoliposomes was added into 1 mL syringe, a pressure of 500 g (measured by a balance) was applied, and a time for different testing samples to completely pass through the membrane with the pore size of 100 nm was recorded. Pure water is taken as a control group, and a ratio of a membrane-through time of other testing samples to a membrane-through time of pure water was calculated to determine the deformability of the nanoliposomes (i.e., the conventional nanoliposomes and the flexible nanoliposomes).

Measurement results: the ratio of the membrane-through time of the conventional nanoliposomes to the membrane-time of the pure water is 156.71%±4.32% (to pass through the membrane with the pore size of 100 nm), and the ratio of the membrane-through time of the flexible nonoliposomes to the membrane-time of the pure water is 139.27%±2.06% (to pass through the membrane with the pore size of 100 nm), which indicates that the deformability of the flexible nanoliposomes is much better, and therefore the penetration-enhancing effect is better. When flexible nanoliposomes with an average particle size (i.e., particle sizes) of 80-150 nm is utilized in combination with the sponge spicules, and a combination use of the sponge spicules and the flexible nanoliposomes lead to a better penetration-enhancing effect.

Referring to FIGS. 6A-10C, a ratio of total skin absorption of drugs induced by the group using the sponge spicules and the flexible nanoliposomes group to that induced by the group using the sponge spicules and the conventional nanoliposome is much higher than a ratio of total skin absorption induced the flexible nanoliposomes to that induced by the conventional nanoliposomes. This also indicates there is a synergistic action induced by the combination use of the sponge spicules and the flexible nanoliposomes.

The aforementioned embodiments are merely some embodiments of the present disclosure, and the scope of the disclosure of is not limited thereto. Thus, it is intended that the present disclosure cover any modifications and variations of the presently presented embodiments provided they are made without departing from the appended claims and the specification of the present disclosure.

What is claimed is:

1. A skin penetration enhancing composition, comprising:
sponge spicules, and
nanoparticles, wherein:
the sponge spicules are derived from *Haliclona* sp., and
the nanoparticles comprise flexible nanoliposomes and at least one of:
one or more drugs, or
one or more cosmetic active ingredients.

2. The skin penetration enhancing composition according to claim 1, wherein: the nanoparticles further comprise nanocarriers comprising at least one of the one or more drugs or the one or more cosmetic active ingredients, or the nanoparticles further comprise nanosized particles of the at least one of the one or more drugs or the one or more cosmetic active ingredients.

3. The skin penetration enhancing composition according to claim 2, wherein the nanocarriers comprise at least one of solid lipid nanoparticles, nanocapsules, nanospheres, polymer micelle, or nanosuspensions.

4. The skin penetration enhancing composition according to claim 1, wherein a purity of the sponge spicules is not less than 90%.

5. The skin penetration enhancing composition according to claim 1, wherein:

the sponge spicules are a sponge spicules suspension, the sponge spicules suspension is utilized in combination with the nanoparticles, the sponge spicules suspension is prepared by at least one of a buffer solution, deionized water, double distilled water, or physiological saline, and a mass concentration of the sponge spicules is from 0.01% to 100%.

6. The skin penetration enhancing composition according to claim 1, wherein the flexible nanoliposomes comprise a surfactant.

7. A method of treatment comprising:

using the skin penetration enhancing composition according to claim 1 for preparing a skin delivery formulation.

8. The method of treatment according to claim 7, comprising:

applying the sponge spicules of the skin delivery formulation to skin after the skin has been cleaned, and applying the nanoparticles of the skin delivery formulation to the skin after applying the sponge spicules to the skin.

9. The method of treatment according to claim 8, comprising:

massaging the skin while applying the nanoparticles.

10. The method of treatment according to claim 9, comprising:

cleaning to remove residual sponge spicules of the skin delivery formulation on a surface of the skin before applying the nanoparticles.

11. The method of treatment according to claim 7, comprising:

directly applying the skin delivery formulation on the skin after the skin has been cleaned.

12. The method of treatment according to claim 11, comprising:

massaging the skin while applying the skin delivery formulation.

* * * * *